United States Patent [19]

Wise et al.

[11] 4,132,672

[45] Jan. 2, 1979

[54] METHANATION CATALYST

[75] Inventors: Henry Wise, Redwood City; Bernard Wood, Santa Clara, both of Calif.

[73] Assignee: American Gas Association, Arlington, Va.

[21] Appl. No.: 771,119

[22] Filed: Feb. 23, 1977

Related U.S. Application Data

[63] Continuation-in-part of Ser. No. 667,104, Mar. 15, 1976, abandoned.

[51] Int. Cl.² .................. B01J 21/04; B01J 23/46; B01J 23/74
[52] U.S. Cl. ................. 252/466 B; 252/472; 260/449.6 M
[58] Field of Search ............ 252/466 B, 466 J, 472; 260/449 M, 449.6 M

[56] References Cited

U.S. PATENT DOCUMENTS

| | | | |
|---|---|---|---|
| 3,271,325 | 9/1966 | Davies et al. | 252/466 B |
| 3,361,535 | 1/1968 | Pollitzer et al. | 260/449 M |
| 3,930,812 | 1/1976 | Harris et al. | 260/449 M |
| 3,953,363 | 4/1976 | Yamauchi et al. | 252/466 B |
| 3,988,334 | 10/1976 | Finch et al. | 252/466 B |

*Primary Examiner*—W. J. Shine
*Attorney, Agent, or Firm*—Howson and Howson

[57] ABSTRACT

An improved method for the conversion of hydrogen and carbon monoxide to a methane-rich gas in which there is employed a supported nickel catalyst promoted by the addition of a small percentage of the iridium metal, typically 0.1 to 1.0% by weight. Said promoted catalyst is highly active for methanation and has good resistance against poisoning by sulfur compounds.

1 Claim, 2 Drawing Figures

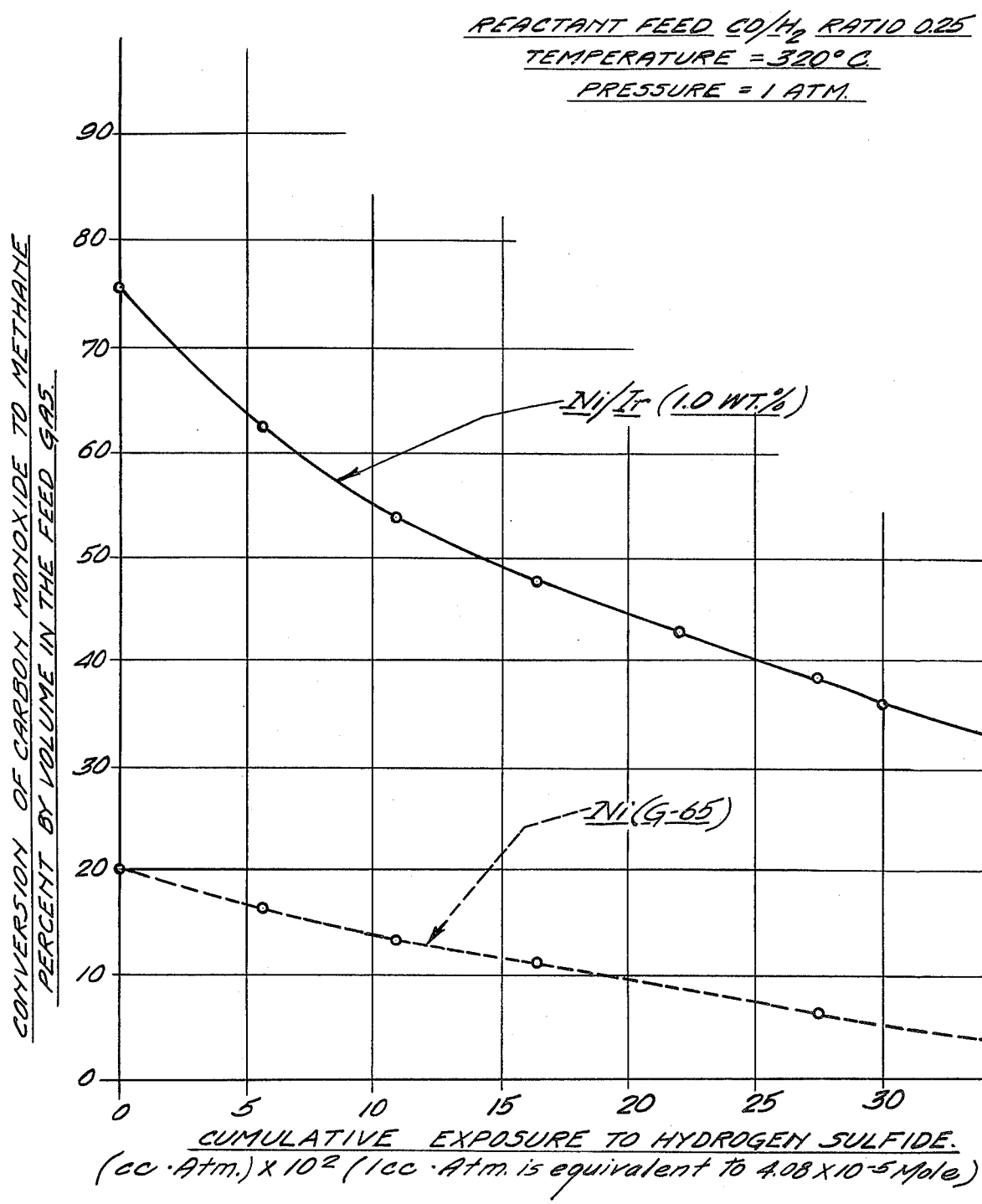

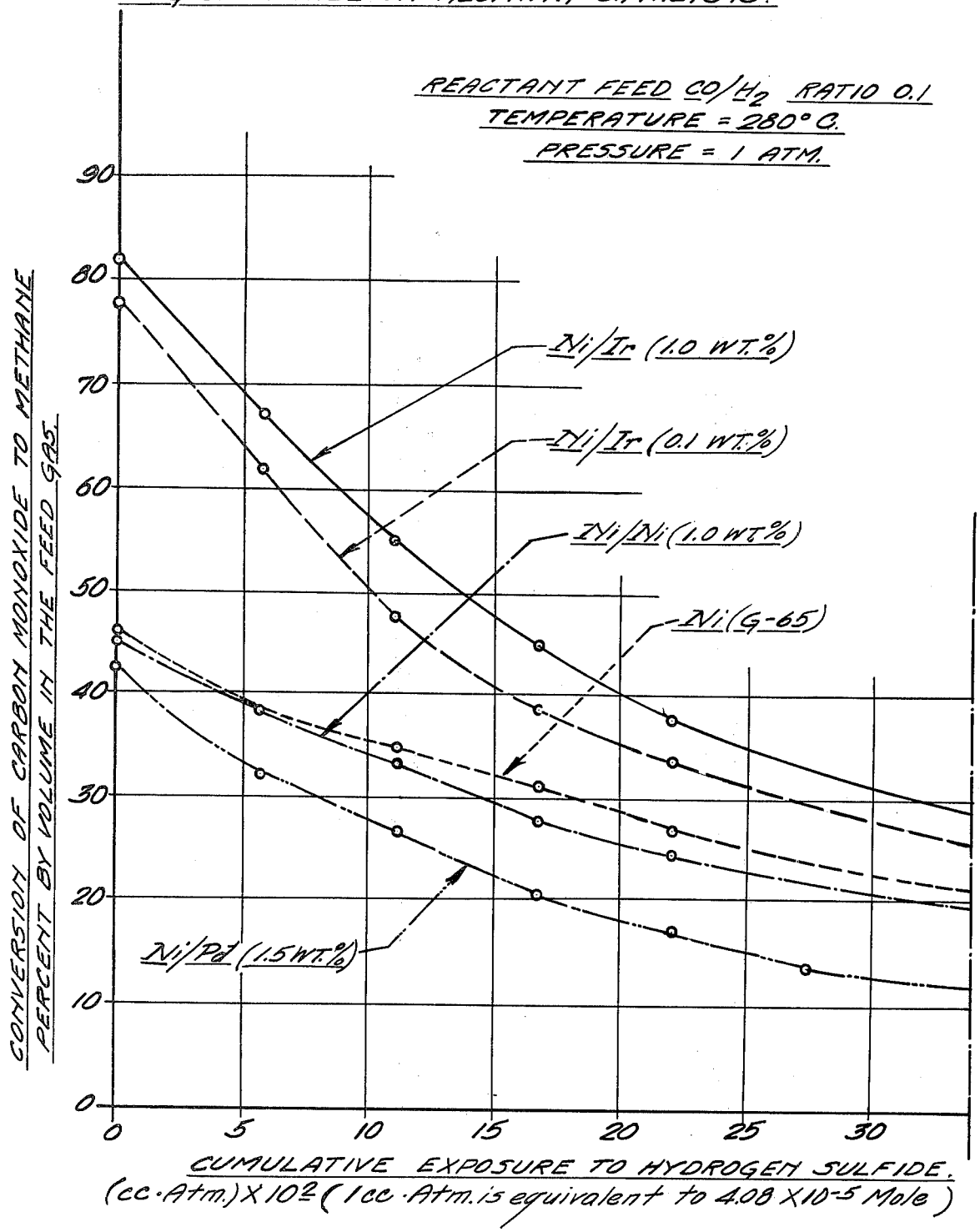

METHANATION CATALYST

This application is a continuation-in-part of our application Ser. No. 667,104 filed Mar. 15, 1976, now abandoned.

BACKGROUND OF THE INVENTION

It has long been desired to find an inexpensive process for the production of a methane-rich gas useful as a substitute for natural gas. Synthetic gas (high Btu SNG) for this purpose should contain at least about 88% methane by volume and be free of the poisonous carbon monoxide. Such gases should also preferably contain less than about two percent hydrogen by volume but may contain inert components such as nitrogen, carbon dioxide and traces of argon.

In 1902 Sabatier and Senderens described the synthesis of methane by the hydrogenation of carbon monoxide. Since that time the hydrogenation of carbon monoxide has been the subject of an extraordinary amount of research and development. However, such processes have not come into widespread use due to the cost of raw materials, low conversion efficiency, and due to the necessity of removing the ever-present sulfur compounds from the feed gas in order to prevent poisoning of the catalyst.

PRIOR ART

A comprehensive summary of the many reactions of carbon monoxide with hydrogen is given in Kirk-Othmer, Encyclopedia of Chemical Technology, Second Edition, Volume 4, pages 446–489, John Wiley and Sons, New York, 1964. It is stated therein at page 452 that "nickel is predominant as a catalyst for synthesis and for reforming of methane according to the reaction:

$$CO + 3H_2 \rightleftarrows CH_4 + H_2O$$

which proceeds from left to right at temperatures below about 500° C. and in the opposite direction at higher temperatures." It is noted further at page 453 that "Metallic Catalysts (Ni, Co, Fe, and Ru), in contrast to oxide catalysts, are extremely sensitive to sulfur compounds, which cause an irreversible contamination especially at low temperatures."

For this reason it has been necessary in the prior art to pass the raw synthesis gas or other feed gas over beds of iron oxide to remove hydrogen sulfide. Organic sulfur compounds such as carbonyl sulfide and carbon disulfide, will still be present in the feed gas, however, and must also be removed. This may be done by passing the gas over a mixture of hydrated iron oxide and sodium carbonate at 200° to 300° C. as described in Kirk-Othmer supra at page 461.

Humphries et al. U.S. Pat. No. 3,511,624 issued May 12, 1970 described a process for making a gas containing a high proportion of methane as a substitute for natural gas by catalytic synthesis from a methane-rich gas produced by the medium temperature gasification of light hydrocarbons in steam. The process comprises passing a mixture of paraffinic hydrocarbons and steam in vapor form at a temperature of 350° C. through a bed of nickel catalyst under atmospheric or superatmospheric pressure so that the exothermic reaction maintains the bed at a temperature of 400° to 550° C. The nickel-alumina catalyst is formed by coprecipitation of nickel and aluminum salts followed by reduction of the nickel to the metallic state. This basic catalyst is promoted by the addition of a minor proportion of an oxide, hydroxide, or carbonate of an alkali or alkaline earth metal. The methane-rich gas formed in this way is then subjected to the action of a nickel catalyst at a lower temperature, e.g. 400° C. or below, to cause formation of methane by reaction between carbon dioxide, carbon monoxide and hydrogen present in the gas. This process is said to be applicable to the production of methane from feed gases in which carbon dioxide predominates over carbon monoxide, whereas methanation is usually carried out on gases where the reverse is true. The process is carried out in two steps as described.

Baker U.S. Pat. No. 3,615,164 issued Oct. 26, 1971, relates to a method for the selective removal of substantially all carbon monoxide from a mixture of gases including hydrogen and carbon dioxide in an amount greater than the carbon monoxide content. The catalysts employed were ruthenium and rhodium on alumina. Fleming et al. U.S. Pat. No. 3,787,468 discloses a similar process employing catalysts containing rhodium and ruthenium and alloys thereof with platinum, beneficiated with admixtures of tungsten oxide.

Ichikawa et al. U.S. Pat. No. 3,842,113, issued Oct. 14, 1974 describes a process for converting carbon dioxide into hydrocarbons and oxygen-containing hydrocarbons employing a catalyst containing at least one alkali metal of Group IA of the Periodic Table, graphite, and at least one halide of a transition metal selected from the group consisting of Groups VIB and VIII of the Periodic Table. The alkalie metal employed in the specific examples was metallic potassium. The graphite was reacted with a chloride of molybdenum, tungsten, cobalt, nickel, palladium, platinum and iron as shown in Tables I and II to form a graphite-transition metal halide interlayer complex before addition of the potassium metal. No mention is made of the use of an iridium halide.

Pruett et al. U.S. Pat. No. 3,833,634 issued Sept. 3, 1974 relates to a process for the preparation of polyfunctional oxygen-containing compounds, such as ethylene glycol, by the hydrogenation of an oxide of carbon using a rhodium complex catalyst. Synthesis gas, a mixture of hydrogen and carbon monoxide in a molar ration of 1:1, was reacted at 1500 atmospheres pressure in tetrahydrofuran with tetrairidium dodecacarbonyl as the catalyst in Example 14 without formation of any of the desired polyhydric alcohols.

Ichikawa et al. U.S. Pat. No. 3,842,121 issued Oct. 15, 1974 relates to catalyst for converting carbon monoxide into hydrocarbons which comprise at least one alkali metal, graphite, and at least one halide of a transition metal selected from the group consisting of Groups IVB, VB, VIB, VIIB, and VIIIB of the Periodic Table. It is stated that all three of the recited ingredients are necessary, and that if only two are employed, the formation of hydrocarbon is extremely low. Iridium is a relatively poor methanation catalyst. (See Vannice, The Catalytic Synthesis of Hydrocarbons from $H_2/CO$ Mixtures over the Group VIII Metals, J. of Catalysis, 37, 449–473.) There is nothing in the Ichikawa et al. patent which illustrates the use of iridium in combination with nickel or any other transition metal. Indeed, due to the poor results obtained with iridium alone, the teachings of the prior art would appear to be against its usage either alone or in combination with other transition metals, including nickel.

Muller U.S. Pat. No. 3,854,895 issued Dec. 17, 1974 relates to a process for producing methane-rich gas useful in place of natural gas involving six separate steps. The methanation of a gas containing carbon monoxide and hydrogen is carried out over hydrogenation catalysts containing elements of the iron group and/or platinum group, i.e. iron, cobalt, nickel, platinum, palladium and the like, on a ceramic, heat-resistant and watervapor-proof support material. Catalysts containing nickel, which contain aluminum oxide, aluminum silicate or magnesium silicate as the support material are said to be particularly suitable. It is noted, however, that such catalysts are sensitive to catalyst poisons and for this reason one of the six steps of the complex method is purification of the feed gas to remove catalyst poisons prior to the methanation step.

It should be apparent from the foregoing that while the production of a methane-rich gas as a substitute for natural gas has long been desired and much work has been done on the hydrogenation of a carbon monoxide for this purpose, no satisfactory (simple), economic and commercially feasible process has as yet been developed for this purpose.

It is, therefore, a primary object of this invention to provide an improved process for the methanation of a gas containing hydrogen and carbon monoxide to provide a methane-rich gas suitable as a substitute for natural gas.

Another primary object of this invention is to provide an improved supported metallic nickel catalyst which is highly active for methanation and has good resistance against poisoning by sulfur-containing compounds.

It is another object of this invention to provide a methanation process such as the foregoing of markedly increased efficiency.

It is still another object of the invention to reduce the degree of needed removal of sulfur containing catalyst poisons from the feed gas prior to methanation.

The foregoing and other objects of the invention will become apparent from the following description thereof.

SUMMARY OF THE INVENTION

The present invention relates to an improved method for conversion of a gas containing hydrogen and carbon monoxide to a methane-rich gas in which there is employed a supported nickel catalyst promoted by the addition of a small amount of iridium metal. This novel catalyst is highly active for methanation in such method and is highly resistant to poisoning by sulfur-containing compounds. Typically the improved supported nickel catalyst contains from about 0.1 to about 1% of metallic iridium by weight of the total catalyst, including the support.

THE DRAWINGS

In the following detailed description, reference will be had to the drawings in which:

FIG. 1 is a graphical representation of the effect of the iridium promoter on the methanation activity and hydrogen sulfide poisoning of nickel on alumina catalyst; and FIG. 2 is a graphical representation of the effect of different promoters on the methanation activity and hydrogen sulfide poisoning of nickel on alumina catalyst.

DESCRIPTION OF THE INVENTION

The present invention is based upon the surprising discovery that the addition of a small amount of metallic iridium to a supported nickel methanation catalyst containing about 10 to 30% nickel increases the methanation activity and also renders the same more resistant to poisoning by sulfur compounds to which the catalyst may be exposed. The amount of iridium metal incorporated in the catalyst should be that which is effective to provide the desired sulfur resistivety and enhancement of methanation efficiency. While this amount will vary from one supported nickel catalyst to another, good results with a wide variety of supported nickel catalysts can be obtained by using from about 0.1 to 1% of metallic iridium based on the total catalyst weight. Improved results can also be obtained in most cases even when using iridium in amounts smaller than 0.1 weight percent, e.g., 0.05 weight percent or even lower. Further, amounts of iridium in excess of 1%, typically up to about 10 weight percent, are also effective. Thus, catalysts of this invention may have an iridium content of from about 0.05% to about 10%. However, increasing the iridium content above 1% is only marginally effective and has the disadvantage of increasing catalyst costs without providing commensurate benefits. A particularly preferred catalyst has a nickel content of about 25% and an iridium content of from about 0.1 to 1.0%.

Any known supported metallic nickel methanation catalyst may be employed as the basis for the improved catalysts of the present invention. Further, any known support material may be employed which does not interfere with the reaction, and may be employed in any conventional form, such as pellets, cylinders, spheres or other geometric shapes adapted to expose a substantial surface area of the metallic nickel catalyst to the gases to be reacted. The supported nickel catalyst may be prepared by any suitable technique, many of which are known to the art. For example, the support material, such as alumina, in any of the conventional shapes, may be wetted with an aqueous solution containing a suitable concentration of any suitable soluble nickel salt. Suitable nickel salts include nickel formate, nickel acetate, the preferred nickel nitrate, or any other salt (not a catalyst poison) sufficiently soluble to give a concentration in water which will provide a minimum of about 10% nickel on the support after drying and reduction.

Inasmuch as it is desired to impregnate the support to provide from about 10 to about 30% metallic nickel in the finished catalyst, the aqueous solutions should contain about 6 to about 20 moles/liter of nickel. Multiple sequential impregnations may be carried out to reach the desired nickel metal weight loading. Suitable porous catalyst supports known to the art include, without limitation, alumina, silica-alumina, aluminum silicate, magnesium silicate, silica gel, activated charcoal, magnesia, titania, zirconia, zeolites and zeolitic molecular sieves, pumice, kieselguhr, inert porous organic polymers, and the like. The catalyst support, impregnated with the solution of nickel salt, is then dried in air, e.g. at 120° C., or under vacuum if desired, or in any other suitable way, to obtain nickel salt impregnated support. The nickel salt impregnated support is then heated in air at temperatures high enough to decompose the nickel salt. When the impregnant is nickel nitrate, temperatures of about 250°-350° C. maintained for a period of about 1 to 5 hours are sufficient to decompose the salt to form nickel oxide with the evolution of nitrogen dioxide. In any event the impregnated support should be heated high enough and long enough to convert substantially all of the original nickel salt to nickel oxide.

Subsequently the nickel oxide-containing support is exposed to hydrogen at temperatures in the range from about 300° to about 500° C. for about 15 to about 20 hours, until substantially all of the nickel oxide has been reduced to metallic nickel.

The foregoing procedure typifies the production of supported metallic nickel catalysts but is not critical to the present invention since any supported metallic nickel methanation catalyst may be employed in a practice of the present invention. Indeed, many suitable catalysts are available commercially such as Girdler G-65 among others, the composition of which is known to be: 25% Ni, 60.5% $Al_2O_3$, 1.0% $SiO_2$, 7.7% CaO, 0.12% MgO, 0.20% $Na_2O$, 4.7% Carbon, all by weight of the catalyst.

If desired, the iridium promoter may be incorporated in the new catalysts at the same time the nickel is added to the support. For example, a nickel salt, such as the nitrate, may be dissolved in water with a suitable soluble iridium salt, such as iridium tetrachloride or potassium hexachloroiridate or ammonium hexachloroiridate in the necessary concentrations to provide the desired metal loading on the catalyst. Typically the iridium salts are dissolved in the impregnating solutions at concentrations of about 0.015 to about 1.5 mole/liter to provide the desired loading on the support.

In the preferred procedure for producing the new catalyst, however, the nickel salt is added first, dried, and oxidized to nickel oxide on the catalyst support before the iridium promoter is added. When this is done, the soluble iridium salt is then added in aqueous solution in the concentrations set forth above and the wet iridium impregnated supported nickel material is dried over a steam bath with continuous stirring to insure uniform distribution of the iridium salt.

The iridium salt is then reduced by any suitable means, the preferred method being to immerse the nickel-iridium salt-impregnated support material into a basic solution of hydrazine. Such a reducing solution may contain from about 1 to about 10 weight percent hydrazine or other reducing agent in about 1 to about 4 weight percent aqueous sodium hydroxide, preferably about 5 weight % hydrazine in 0.5 normal sodium hydroxide. Other suitable reducing agents include sodium borohydride. The resulting mixture is stirred gently for about 24 hours to assure substantially complete reduction of the iridium salt to the metallic state on the support.

The reduced mass is then washed repeatedly with boiling water until substantially all of the soluble anions have been removed. The catalyst is then thoroughly dried for example, by heating to about 100° to about 125° C. for about 1 to about 100 hours. The drying is suitably accomplished in a vacuum at a temperature of about 60° C., for about 96 hours.

The resulting catalyst is conditioned prior to use by heating at a temperature of from about 350° to about 500° C. for about 4 to about 20 hours under hydrogen at a pressure of from about 1 to about 2 atmospheres. The preferred procedure is to heat the catalyst at 400° to 450° C. under a stream of hydrogen for 3 to 4 hours at atmospheric pressure.

The catalyst is then ready for use according to conventional procedures to convert gases containing hydrogen and carbon monoxide to methane-rich gases suitable for use as a substitute for natural gas.

More specifically, the new catalysts may be used with advantage to methanate virtually any gas containing hydrogen and carbon monoxide. As a practical matter, however, the feed gas should have a carbon monoxide to hydrogen volume/volume ratio of at least about 0.001 and this ratio may range up to about 0.33; i.e. one volume of carbon monoxide to 3 volumes of hydrogen, which expressed otherwise, would be 25% by volume of carbon monoxide and 75% by volume of hydrogen, if the gas contained only these two ingredients, equivalent to the stoichiometric ratio of carbon monoxide to hydrogen in a mixture of the two gases.

The present methanation process is of the low temperature type, since as noted above, the reaction of carbon monoxide with hydrogen to form methane is reversible above 550° C. Generally speaking the catalysts of the present invention provide efficient methanation at temperatures of about 150° to about 350° C. and are normally employed at temperatures of about 200° to about 350° C., preferably about 280° C.

The methanation reaction may be carried out at elevated pressures but little advantage is seen in doing so inasmuch as very high efficiencies are obtained at atmospheric pressure so there is no need to entail the cost of pressure equipment.

The new catalysts have been found to exhibit a much higher conversion efficiency than unpromoted nickel catalysts of the prior art, and also to be surprisingly resistant to poisoning by sulfur, sulfur compounds and other catalyst poisons, as will become apparent from the following specific examples and data.

EXAMPLE I

A catalyst of the present invention was prepared starting with a commercial methanation catalyst, Girdler G-65, available from Girdler Catalysts Department, Chemetron Chemicals Division, Chemetron Corp. This catalyst consists essentially of a pelletized alumina support on which is deposited as a principal ingredient, metallic nickel in an amount equivalent to about 25% by weight of the total catalyst. This material was crushed and screened to produce a particulate base catalyst of about 14 to 20 mesh screen. This material was then impregnated using about 0.35 ml/g of a 0.15 molar aqueous solution of potassium hexachloroiridate ($K_2IrCl_6$). The moist mixture was then dried over a steam bath with continuous stirring to ensure uniform distribution of the iridium salt on the nickel catalyst.

The dry iridium salt-impregnated material obtained in this way was then immersed in a solution containing 5% by weight of hydrazine in 0.5 normal sodium hydroxide. This mixture was stirred for 5 minutes and allowed to stand at room temperature for 24 hours until substantially all of the iridium salt on the support had been reduced to metallic iridium.

The reduced material was then washed repeatedly with boiling water until substantially all of the soluble anions had been removed. The washed mass was then dried by heating to 60° C. in a vacuum over at 50 mm/Hg pressure for about 96 hours to produce the desired catalyst. In this way a catalyst was prepared consisting of an alumina support with 25% by weight of metallic nickel and 1.0% by weight of metallic iridium based on the weight of the total catalyst.

The catalyst was heated to a temperature of about 450° C. under a stream of hydrogen at atmospheric pressure for 15 hours prior to use. The thus activated catalyst was then employed as a catalyst bed in a methanation apparatus and a stream of feed gas was passed through it at the rate of 6 liters per hour at atmospheric pressure and a temperature of 320° C. The feed gas consisted of carbon monoxide and hydrogen in a ratio of 1:4, i.e. 0.25, or 20% carbon monoxide, by volume of the mixed gas. The feed gas also contained 55 ppm (parts per million) of hydrogen sulfide, by volume of the gas as a whole, which was added to test the resistance of the catalyst to this catalyst poison. For purposes of comparison the unpromoted nickel-alumina Girdler G-65 catalyst was tested under identical conditions. The cumulative amount of hydrogen sulfide exposure and the degree of conversion of carbon monoxide to methane were recorded at fixed intervals (every 10 minutes) for each of the two catalysts and the results set forth in Table I below and plotted in FIG. 1 of the drawings. The cumulative exposure of hydrogen sulfide was measured in cubic centimeters (cc) times atmospheric and muptiplied by 100; one cc atm. being equivalent to $4.08 \times 10^{-5}$ mole multiplied by 100. The methanation activity of the two catalysts under these conditions was measured as the percentage of the carbon monoxide in the feed gas converted to methane at the various intervals.

Table I

Effect of Iridium Promoter on the Methanation Activity and Resistance to Poisoning of a Nickel on Alumina Methanation Catalyst

| Cumulative H$_2$S Exposure (cc atm) × 10$^2$ | Conversion to Methane (vol. %) | |
|---|---|---|
| | Ni/Ir (1 wt %) | Ni (G-65) |
| 0 | 76 | 20 |
| 5.5 | 62.5 | 16.5 |
| 11.0 | 54 | 13.5 |
| 16.5 | 48 | 11.5 |
| 22.0 | 43 | — |
| 27.5 | 39 | 6.5 |
| 30.0 | 36.5 | |

Referring to FIG. 1 of the drawings it will be seen that the initial methanation activity of the iridium promoted catalyst of the invention provided about 76 volume % conversion of carbon monoxide in the feed to methane as compared to 20 volume % conversion for the same nickel-on-alumina catalyst without the iridium promoter under these conditions. As the methanation proceeded and the two catalysts were exposed to cumulatively greater amounts of hydrogen sulfide, the methanation activity of each catalyst declined until at 27.5 × 10$^{-2}$ cc/atm hydrogen sulfide exposure, the activity of the unpromoted catalyst had fallen to provide only 6.5 volume % conversion of the carbon monoxide. While the activity of the iridium promoted catalyst also declined, at the 27.5 × 10$^{-2}$ cc/atm hydrogen sulfide exposure level it still provided 39 volume % conversion of the carbon monoxide. It will be seen, therefore, that under both the initial unpoisoned condition and under the final poisoned condition, the methanation activity of the iridium promoted catalyst was about four times that of the unpromoted catalyst. Moreover, even the poisoned promoted catalyst remained twice as active as the unpoisoned unpromoted catalyst.

EXAMPLE II

In order to illustrate further the superiority of the iridium promoted catalysts of the invention over familiar catalysts of the prior art, the procedure of Example I was repeated using the same commercial 25% nickel-on-alumina catalyst. Girdler G-65, as the basis for a series of catalysts. The catalyst was ground and size graded as before to 14-20 Tyler mesh and then four samples were wet with 0.035 ml/g of aqueous solutions containing respectively: (1) and (2) 0.15 and 0.015 mole/liter of potassium hexachloroiridate (K$_2$IrCl$_6$); (3) 0.15 mole/liter of nickel chloride (NiCl$_2$.6H$_2$O); and (4) 0.23 mole/liter of sodium tetrachloro palladate (Na$_2$PdCl$_4$); said concentrations being calculated to provide final dry catalysts containing 1 and 0.1 weight % iridium; 1 weight % added nickel; and 1.5 weight % palladium; respectively. A fifth sample of the ground basic catalyst was also included in the series without any added promoter. The four different wet catalyst masses were dried as before on a steam bath with stirring. The dried mixtures were then separately immersed in a 5.0% solution of hydrazine in 0.5 N sodium hydroxide and reduced as in Example 1. The five different catalysts were activated as in Example I by heating at 450° C. for 15 hours under a stream of hydrogen at atmospheric pressure.

The five different catalysts were then tested for methanation activity and resistance to hydrogen sulfide poisoning under identical conditions according to the general procedure of Example I. The feed gas consisted of carbon monoxide in hydrogen at a ratio of about 0.1 by volume, i.e. one part of carbon monoxide and 9 parts of hydrogen. The feed gas also contained about 55 ppm of added hydrogen sulfide as before to test the resistance of the catalysts to sulfur poisoning.

Table II

Comparison of Iridium Promoted Nickel Catalysts With Unpromoted and Palladium Promoted Nickel Catalysts as to Methanation Activity and Resistance to Poisoning

| Cumulative H$_2$S Exposure (cc atm) × 10$^2$ | Conversion to Methane (vol %) | | | | |
|---|---|---|---|---|---|
| | Ni/Ir (1%) | Ni/Ir (0.1%) | Ni/Ni (1%) | Ni/Pd (1.5%) | Ni (G-65) |
| 0 | 82 | 78 | 45 | 42.5 | 46 |
| 5.5 | 67.5 | 62 | 39 | 32.5 | 39 |
| 11.0 | 55 | 48 | 33 | 27 | 35 |
| 16.5 | 45 | 39 | 28 | 20.5 | 31 |
| 22.0 | 38 | 34 | 24.5 | 17.5 | 27 |
| 27.5 | — | — | — | 14 | — |

As noted above, all of the five catalysts compared in this Example were basically commercially available Girdler G-65 catalyst which consists of an alumina support on which is deposited 25% of metallic nickel, based on the weight of the nickel and alumina taken together. This material was then divided into five samples, one of which was treated no further. Two of the samples were impregnated with iridium as described above to provide catalysts containing 1.0% and 0.1% iridium metal promoter respectively. A fourth sample was impregnated with a palladium salt to provide a finished catalyst containing 1.5% by weight of metallic palladium as a promoter for the nickel. In order to determine whether or not the improvement exhibited by the catalysts of the invention was simply due to increased loading of catalyst metal, a fifth sample of the basic catalyst was treated to add an additional 1.0% by weight of nickel to the 25% already present. Therefore, the total weight of nickel metal on the support was equivalent to the total weight of nickel and iridium promoter in the 1.0% iridium promoted catalyst.

The data in Table II above are plotted in FIG. 2 of the accompanying drawing wherein the relative methanation activity and resistance to hydrogen sulfide poisoning of the five catalysts may be clearly seen. It will be noted that the palladium promoted catalyst was the poorest performer, failing to equal the activity of the basic unpromoted nickel on alumina catalyst. It will also be seen that the additional 1.0% by weight of nickel added to the basic catalyst not only did not improve its activity, but slightly worsened its resistance to poisoning.

The catalyst promoted by the addition of 1.0% by weight of iridium provided initial conversion of 82% of the carbon monoxide compared to only 46% for the unpromoted catalyst and 45% and 42.5%, respectively, for the catalyst with added nickel and the palladium promoted catalyst. Even after exposure to $22.0 \times 10^{-2}$ cc/atm of hydrogen sulfide, the 1.0% iridium promoted catalyst was still able to convert 38% of the carbon monoxide, against only 24.5%, 17.5% and 27% conversions for the nickel promoted, palladium promoted and unpromoted nickel on alumina catalyst. It is apparent, therefore, that the iridium promoted catalyst is markedly superior to the others tested.

The 0.1% iridium promoted catalyst was almost as active as the 1.0% iridium promoted catalyst and was also markedly superior to the nickel promoted, palladium promoted and unpromoted nickel on alumina catalysts.

The data in Tables I and II and corresponding FIGS. 1 and 2 are not directly comparable because the methanation reactions were run at different temperatures, and because the ratio of carbon monoxide to hydrogen in the feed gas also differed. However, by comparing the curves for the 1.0% iridium promoted catalyst in FIGS. 1 and 2, it seems clear that the resistance to hydrogen sulfide poisoning of such a catalyst is increased at higher temperatures and higher ratios of carbon monoxide to hydrogen. It is believed that this may be due to a significant rate of sulfur removal from the surface of the catalyst of hydrogen under these conditions.

EXAMPLE III

The general procedure of Examples I and II above was used to prepare a catalyst derived from the Girdler G-65, 25% nickel on alumina catalyst, promoted with 1.2% by weight of platinum metal. This catalyst was compared to the 1.0% iridium promoted catalyst described above by methanation of a feed gas having a carbon monoxide to hydrogen percentage volume ration of 0.1, and containing 55 ppm of hydrogen sulfide as before, at a temperature of 280° C. under one atmosphere pressure, absolute. The data are set forth in Table III below.

Table III

Methanation Activity and Resistance to Hydrogen Sulfide Poisoning of Platinum and Iridium Promoted Nickel Catalysts

| Cumulative $H_2S$ - Exposure (cc · atm) $\times 10^2$ | Conversion to Methane (vol. %) | |
|---|---|---|
| | 1 Wt % Ir | 1.2 Wt % Pt |
| 0 | 82 | 64 |
| 5.5 | 66 | 48 |
| 11 | 56 | 38 |

It will be seen that the initial activity of the 1.0% iridium promoted catalyst was sufficient to convert 82% of the carbon monoxide in the feed gas to methane against only 64% for the platinum promoted catalyst which contained more promoter. Therefore, the iridium promoted catalyst when fresh was about 28% more active than the platinum promoted catalyst. Even more surprisingly, after exposure to $11 \times 10^{-2}$ cc . atm of hydrogen sulfide the iridium promoted catalyst was still able to convert 56% of the carbon monoxide in the feed gas against only 38% for the platinum catalyst, an improvement of 47% in activity.

Although many suitable nickel on alumina catalysts are available commercially to serve as a basis for the preparation of the iridium promoted catalysts of the present invention, the preparation of such catalyst will now be described. A suitably shaped alumina support in any desired form such as pellets, cylinders, or spheres, is impregnated with an aqueous solution containing a soluble nickel salt such as nickel nitrate, for example, at a concentration calculated to provide the desired weight loading of nickel on the finished catalyst. The wetted support containing the nickel salt is then dried in air, for example at 120° C. The resulting dried material is then heated to a temperature sufficiently high to decompose the nickel salt. In the case of nickel nitrate, the salt will break down to nickel oxide with evolution of nitrogen dioxide at temperatures in the range from about 250° to about 350° C. The nickel oxide on the alumina support may then be reduced by exposure to hydrogen at temperatures in the range from about 300° to 500° C. In this way a metallic nickel on alumina catalyst having some methanation activity and suitable for promotion according to the present invention may be obtained. Any suitable support other than alumina may be used in the same way, e.g. kieselguhr, silica, kaolin and the like. The nickel loading may suitably vary from about 10 to about 30% by weight of the catalyst, about 25% being preferred. Other catalyst components may include calcium oxide, carbon, sodium oxide, and magnesium oxide. Such a supported nickel catalyst may be impregnated as above by the use of any suitable soluble iridium salt and then reduced to provide iridium metal at a loading of from about 0.1 to about 1% by weight of the catalyst and activated by hydrogen reduction prior to use as described above.

What is claimed is:

1. A catalyst for the conversion of carbon monoxide and hydrogen to methane consisting essentially of a porous alumina support carrying about 25 percent by weight of metallic nickel catalyst together with from about 0.1 to about 1 percent by weight of iridium, said catalyst having been prepared by depositing the metallic nickel catalyst on the alumina support, impregnating the supported metallic nickel catalyst with an aqueous solution of a water soluble salt of iridium, converting said salt to metallic iridium, and heating the resulting catalyst at a temperature of from about 350° to about 500° C. in the presence of hydrogen for about 4 to about 20 hours.

* * * * *